United States Patent [19]

Gil et al.

[11] Patent Number: 4,569,999

[45] Date of Patent: Feb. 11, 1986

[54] 2-SUBSTITUTED-3-SULFONAMIDE-PYRIDINE DERIVATIVES

[75] Inventors: M. Carmen G. Gil; Vicente G. Parra; Félix S. Alonso; Tomás T. Cebada, all of Madrid, Spain

[73] Assignee: Fabrica de Productos Quimicos y Farmaceuticos Abello, S.A., Madrid, Spain

[21] Appl. No.: 626,959

[22] Filed: Jul. 2, 1984

[30] Foreign Application Priority Data

Jul. 6, 1983 [ES] Spain .................................... 523.901

[51] Int. Cl.$^4$ .................. C07D 412/12; C07D 405/12
[52] U.S. Cl. .................................... 546/275; 546/283; 546/293
[58] Field of Search ..................... 546/283, 293, 275

[56] References Cited

U.S. PATENT DOCUMENTS

| | | | |
|---|---|---|---|
| 3,480,640 | 11/1969 | Wilhelm et al. | 546/275 |
| 4,091,104 | 5/1978 | Baldwin | 546/275 |
| 4,092,419 | 5/1978 | Baldwin | 546/275 |
| 4,096,151 | 6/1978 | Baldwin | 546/275 |
| 4,115,575 | 9/1978 | Frei et al. | 546/275 |

*Primary Examiner*—Jane T. Fan
*Attorney, Agent, or Firm*—William H. Nicholson; Michael C. Sudol

[57] ABSTRACT

2-Substituted-3-sulfonamidepyridine derivatives useful as hypotensives and as alpha and beta adrenergic blocking drugs as well as intermediates in the synthesis of other pharmacologically active pyridines. A process for preparing said derivatives is also described.

11 Claims, No Drawings

2-SUBSTITUTED-3-SULFONAMIDE-PYRIDINE DERIVATIVES

The present specification describes a process for preparing 2-substituted-3-sulfonamidepyridine derivatives of general formula I

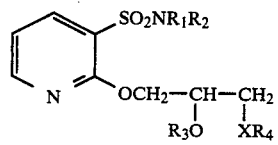

wherein $R_1$ and $R_2$ represent a hydrogen atom or a lower alkyl group, $R_3$ and $R_4$ are hydrogens or else form a five-membered ring with two substituents $R_5R_6C>$, wherein $R_5$ and $R_6$ are independently hydrogen, lower alkyl group, phenyl or heteroaryl group, which substitution is optional, and X represents an oxygen atom or a $<N-R_7$ group, $R_7$ being a $C_1-C_6$ alkyl group preferably branched out with isopropyl, isobutyl, t-butyl, isoamyl, t-amyl, neo-pentyl or another similar one.

The compounds referred to this invention as well as the intermediate compounds for their preparation have an interest because of their therapeutic use as hypotensives and as alpha and beta adrenergic blocking drugs, and also as intermediates for the synthesis of other active pyridines in pharmacology.

According to this invention the compounds of general formula I are prepared through one or two steps from the pyridines of general formula II as it is depicted in the next scheme:

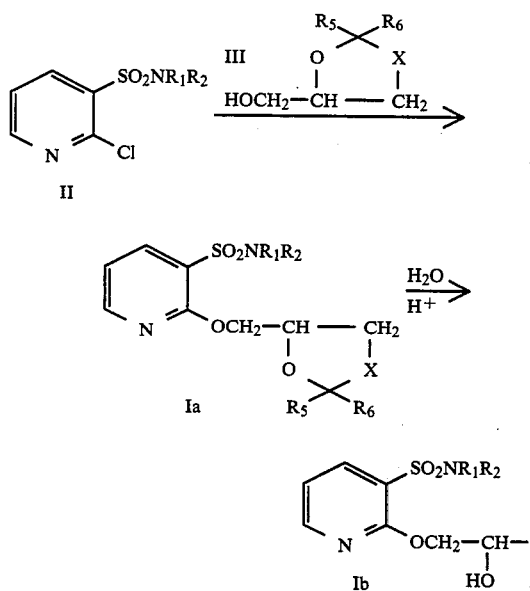

The first step comprises reacting a compound of general formula II, prepared through a modification of the original procedure [L. Thunus, *Annales Pharm. Franc.*, 32(6), 377 (1974)], with an alcohol of general formula III

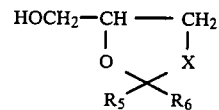

under a liquid-liquid phase transfer conditions, using a water-inmiscible lipophilic solvent as organic phase, such as benzene, toluene, xylene, methylene chloride, chloroform, chlorobenzene, etc., and a solution of an alkali metal or alkaline-earth hydroxide, carbonate or bicarbonate as aqueous phase, or also using the solid-liquid phase-transfer catalytic conditions, the solid phase being a finely ground alkali metal or alkaline-earth hydroxide, carbonate or bicarbonate and the liquid phase a polar or apolar solvent such as ethyl ether, acetonitrile, toluene, etc.; using in both cases a catalyst such as aliquat 336, tetrabutylammonium bromide, benzyltrimethylammonium bromide, benzyltrimethylphosphonium chloride or other similar, stirring at a rate higher than 350 rpm, keeping a temperature within the range of about 25° to 140° C. and for a period of 2 to 24 h, according to the cases. Products of general formula Ia are obtained and purified through column chromatography with a suitable solvent or by crystallization.

Alternatively, the first reaction step is carried out reacting an alcohol of general formula III with an alkali metal or alkaline-earth hydride, without any solvent or in a solvent with a very strong solvation such as dimethylformamide, dimethylacetamide, hexamethylphosphoric triamide (HMPT), etc., and then with a derivative of general formula II in a similar solvent, at a temperature within the range of about 25° to 180° C., for a period of 1 to 24 h, according to the cases. After the usual treatment, the compounds of general formula Ia are obtained.

For preparing the derivatives of general formula Ib, in the second reaction step the products of general formula Ia are treated with a diluted mineral or organic acid, kept at a temperature within the range of about 20° to 110° C. and for a period of 10 min to 10 h. Derivatives of general formula Ib, that are isolated through column chromatography with a suitable eluent or by crystallization, are obtained as bases or salts of a mineral or organic acid, in accordance with the treatment used.

The following examples illustrate the processes used for preparing the 2-substituted-3-sulfonamidepyridines, that are claimed in this specification, and are not intended to limit the scope of this invention.

EXAMPLE 1

2-(O,O-isopropyliden-2,3-dihydroxypropoxy)-3-sulfonamidepyridine

To a solution of 12 g (0.091 mole) of isopropylidenglycerol dissolved in 50 mL of anhydrous dimethylformamide, 3.9 g (0.13 mole) of 80% sodium hydride are added. The mixture is heated, stirred and kept at 90° C. for 30 min until complete solution of the metallic hydride. Then 17 g (0.088 mole) of 2-chloro-3-sulfonamidepyridine are added at once, and the mixture is heated at 90° C. for 5 hours. The reaction being finished, the mixture is poured into 500 mL of an ice-water mixture and extracted with ethyl acetate (5×150 mL). The organic phase is concentrated "in vacuo" and a thick oil is obtained. The product was chromatographed on silica gel and crystallized from ethyl acetate-n-hexane. m.p. 127°–128° C. 12.95 g (51%) yield.

Analysis for $C_{11}H_{16}N_2O_5S$: Theory %: C 45.82; H 5.59; N 9.72; S 11.12. Found %: C 46.08; H 5.84; N 9.90; S 11.45.

Ir (KBr): $\bar{\nu}$ (cm$^{-1}$) 3330, 3220, 1584, 1570, 1429, 1340, 1168.

$^1$H-Nmr (CDCl$_3$): δ (ppm) 8.30, 8.13 (2dd, 2H, 4—C$\underline{H}$, 6—C$\underline{H}$); 7.03 (dd, 1H, 5—C$\underline{H}$); 5.78 (broad peak, 2H, SO$_2$N$\underline{H}_2$); 4.9–3.9 (m, 5H, OC$\underline{H}_2$C$\underline{H}$C$\underline{H}_2$); 1.48, 1.37 (2s, 6H, C$\underline{H}_3$).

EXAMPLE 2

2-(O,O-isopropyliden-2,3-dihydroxypropoxy)-3-N,N-dimethylsulfonamidepyridine

To a well stirred mixture of 8.82 g (0.04 mole) of 2-chloro-3-N,N-dimethylsulfonamidepyridine, 1.34 g (0.004 mole) of tetrabutylammonium bromide, 50 mL of toluene and 20 mL of a solution of 50% sodium hydroxide are added 5.84 (0.044 mole) of isopropylideneglycerol in the minimum toluene amount. The mixture is kept at 80° C. and well stirred for 4 hours. When the reaction mixture is cooled the organic and aqueous phases remain inmiscible; the aqueous one is extracted with toluene (2×15 mL). The whole organic extracts are washed with water until neutrality, dried and concentrated "in vacuo". The oily residue is chromatographied on silica gel using acetone-petroleum spirit (2:3) as eluent. 10.5 g of a viscous oil that solidifies by cooling are obtained. m.p. 83°–84° C. (ethyl ether-n-hexane). 83% yield.

Analysis for $C_{13}H_{20}N_2O_5S$: Theory %: C 49.37; H 6.37; N 8.85; S 10.13. Found %: C 49.30; H 6.41; N 8.77; S 10.29.

Ir (alkali halide disc): $\bar{\nu}$ (cm$^{-1}$) 1575, 1560, 1421, 1324, 1143.

$^1$H-Nmr (CDCl$_3$): δ (ppm) 8.50–8.0 (AB part of the ABX system, 2H, 4—C$\underline{H}$, 6—C$\underline{H}$); 7.00 (part X of the ABX system, 1H, 5—C$\underline{H}$); 4.7–3.6 (m, 5H, OC$\underline{H}_2$—C$\underline{H}$—C$\underline{H}_2$); 2.88 (s, 6H, NC$\underline{H}_3$); 1.43, 1.36 (2s, 6H, C$\underline{H}_3$).

EXAMPLE 3

2-(O,O-isopropyliden-2,3-dihydroxypropoxy)-3-N,N-diethylsulfonamidepyridine

To a well stirred mixture of 10 g (0.040 mole) of 2-chloro-3-N,N-diethylsulfonamidepyridine, 1.34 g (0.004 mole) of tetrabutylammonium bromide, 50 mL of toluene and 20 mL of 50% sodium hydroxide are added 5.84 g (0.044 mole) of isopropylideneglycerol. The mixture is vigorously stirred and heated at 80° for 4 hours. From the organic and aqueous separated phases, the aqueous one is extracted with toluene. The organic extracts are washed until neutrality, dried and evaporated "in vacuo". The final oil is purified through flash silica gel column chromatography using acetone-petroleum spirit (2:3) as eluent. 9.9 g of a colourless viscous oily product are obtained. 72% yield.

Analysis for $C_{15}H_{24}N_2O_5S$: Theory %: C 52.31, H 7.02; N 8.13; S 9.31. Found %: C 52.20, H 7.11; N 8.02; S 9.61.

Ir (alkali halide disc): $\bar{\nu}$ (cm$^{-1}$) 1584, 1570, 1430, 1332, 1158.

$^1$H-Nmr (CDCl$_3$): δ (ppm) 8.5–7.9 (part AB of the ABX system, 2H, 4—C$\underline{H}$, 6—C$\underline{H}$); 6.95 (part X of the ABX system, 1H, 5—C$\underline{H}$); 4.7–3.6 (m, 5H, OC$\underline{H}_2$C$\underline{H}$C$\underline{H}_2$); 3.36 (q, 4H, NC$\underline{H}_2$CH$_3$); 1.43, 1.37 (2s, 6H, C$\underline{H}_3$); 1.13 (t, 6H, NCH$_2$C$\underline{H}_3$).

EXAMPLE 4

2-(N,O-benzyliden-2-hydroxy-3-t-butylaminopropoxy)-3-N,N-dimethylsulfonamidepyridine A solution of 4.15 g (0.0176 mole) of (S)-3-t-butyl-5-hydroxymethyl-2-phenyloxazolidine in 7 mL of toluene is added to a well stirred mixture of 3.55 g (0.0161 mole) of 2-chloro-3-N,N-dimethylsulfonamidepyridine, 0.52 g (1.61 mole) of tetrabutylammonium bromide, 7 mL of toluene and 7 mL of an aqueous solution of 50% sodium hydroxide. The reaction mixture is vigorously stirred and kept at 85° C. for 5 hours. From the organic and aqueous separated phases, the aqueous one is extracted with toluene. The whole organic extracts are repeatedly washed with water, dried and evaporated "in vacuo". An oil is obtained and chromatographied on silica gel using petroleum spirit-acetone (3:1) as eluent. 5.94 g of product are obtained as a colourless viscous oil. 80% yield.

Analysis for $C_{21}H_{29}N_3O_4S$: Theory%: C 60.12; H 6.97; N 10.02; S 7.64. Found %: C 60.08; H 7.09; N 9.90; S 7.92.

Ir (alkali halid disc): $\bar{\nu}$ (cm$^{-1}$) 1576, 1560, 1420, 1330.

$^1$H-Nmr (CDCl$_3$): δ (ppm) 8.4–8.0 (part AB of the ABX system, 2H, 4—C$\underline{H}$, 6—C$\underline{H}$); 7.7–7.1 (m, 5—H arom); 6.95 (part X of the ABX system, 1H, 5—C$\underline{H}$); 5.67, 5.59 (2s, 1H, CH—φ of both isomers): 4.7–4.1 (m, 3H, ArOC$\underline{H}_2$C$\underline{H}$); 3.9–2.6 (m, 2H, NC$\underline{H}_2$); 2.83; 2.74 (2s, 6H, NC$\underline{H}_3$ of both isomers); 1.12, 1.09 (2s, 9H, C(C$\underline{H}_3$)$_3$ of both isomers).

EXAMPLE 5

2-(N,O-benzyliden-2-hydroxy-3-t-butylaminopropoxy)-3-N,N-diethylsulfonamidepyridine A solution of 6.23 g (0.0265 mole) of (S)-3-t-butyl-5-hydroxymethyl-2-phenyloxazolidine in 10 mL of toluene is added to a well stirred mixture of 6 g (0.0241 mole) of 2-chloro-3-N,N-diethylsulfonamidepyridine, 0.78 g (2.42 mmole) of tetrabutylammonium bromide, 10 mL of toluene and 10 mL of an aqueous solution of 50% sodium hydroxide. The reaction mixture is vigorously stirred and kept at 85° C. for 5 hours. After the separation of the aqueous and organic phases, the first one is extracted with toluene. The whole organic extractions are repeatedly washed with water until neutrality, dried and evaporated under reduce pressure affording to an oil. This is purified through silica gel column chromatography using petroleum spirit-acetone (3:1) as eluent affording to 7.91 g of the product expected as a colourless viscous oil. 73% yield.

Analysis for $C_{23}H_{33}N_3O_4S$: Theory %: C 61.72; H 7.43; N 9.39; S 7.16. Found %: C 61.50; H 7.45; N 9.36; S 7.50.

Ir (alkali halide disc): $\bar{\nu}$ (cm$^{-1}$) 1583, 1568, 1460, 1430, 1330, 1205.

$^1$H-Nmr (CDCl$_3$): δ (ppm) 8.4–8.0 (part AB of the ABX system, 2H, 4—C$\underline{H}$, 6C$\underline{H}$); 7.7–7.1 (m, 5—H arom); 6.92 (part X of the ABX system, 1H, 5—C$\underline{H}$); 5.65, 5.57 (2s, 1H, CH—φ of both isomers); 4.7–4.1 (m, 3H, OC$\underline{H}_2$C$\underline{H}$); 4.0–2.6 (m, 2H, NC$\underline{H}_2$); 3.20 (q, 4H, NC$\underline{H}_2$CH$_3$); 1.10, 1.07 (2s, 9H, C(C$\underline{H}_3$)$_3$ of both isomers); 0.94 (t, 6H, NCH$_2$C$\underline{H}_3$).

EXAMPLE 6

2-(2,3-dihydroxypropoxy)-3-sulfonamidepyridine 2.88 g (0.01 mole) of 2-(O,O-isopropyliden-2,3-dihydroxypropoxy)-3-sulfonamidepyridine are suspended in 60 mL of 1N hydrochloric acid and 50 mL of ethanol are added. The mixture is stirred at room temperature for 40 min. Then a solution is obtained and washed with chloroform. The aqueous phase is evaporated until dryness and the residue is chromatographied on silica gel affording to 2.13 g of a viscous oil. 86% yield.

Analysis for $C_8H_{12}N_2O_5S$: Theory %: C 38.71; H 4.87; N 11.28; S 12.92. Found %: C 38.82; H 4.95; N 11.20; S 12.98.

Ir (alkali halide disc): $\bar{\nu}$ (cm$^{-1}$) 3300 (very strong), 1580, 1565, 1420, 1320.

$^1$H-Nmr (DMSO-d$_6$): δ (ppm) 8.34, 8.08 (2dd, 2H, 4—C$\underline{H}$, 6—C$\underline{H}$); 7.13 (dd, 5—C$\underline{H}$); 5.9 (broad peak, 4H, SO$_2$N—H$_2$, O$\underline{H}$); 4.7–4.2 (m, 2$\underline{H}$, OC$\underline{H}_2$); 4.2–3.3 (m, 3H, C$\underline{H}$OHC$\underline{H}_2$OH).

EXAMPLE 7

2-(2,3-dihydroxypropoxy)-3-N,N-dimethylsulfonamidepyridine

A mixture of 3.16 g (0.01 mole) of 2-(O,O-isopropyliden-2,3-dihydroxypropoxy)-3-N,N-dimethylsulfonamidepyridine, 30 mL of 1N hydrochloric acid and 20 mL of ethanol are magnetically stirred at room temperature for 1 hour. The reaction mixture is evaporated till dryness and the oily residue is dried under "vacuum" on potassium hydroxide. The crude of the reaction is purified through a short silica gel column chromatography using chloroform-methanol (9:1) as eluent. 2.21 g of the product required are obtained. 80% yield.

Analysis for $C_{10}H_{16}N_2O_5S$: Theory %: C 43.47; H 5.84; N 10.14; S 11.60. Found %: C 43.65; H 5.90; N 10.09; S 11.78.

Ir (alkali halide disc): $\bar{\nu}$ (cm$^{-1}$) 3370 (very strong), 1578, 1562, 1448, 1425, 1330.

$^1$H-Nmr (DMSO-d$_6$): δ (ppm) 8.6–8.0 (part AB of the ABX system, 2H, 4—C$\underline{H}$); 7.16 (part X of the ABX system, 1H, 5—C$\underline{H}$); 5.1 (broad peak, 2H, OH, disappears on adding D$_2$O); 4.7–4.2 (m, 2H, OC$\underline{H}_2$); 4.2–3.3 (m, 3H, C$\underline{H}$OHC$\underline{H}_2$OH); 2.79 (s, 6H, NC$\underline{H}_3$).

EXAMPLE 8

2-(2,3-dihydroxypropoxy)-3-N,N-diethylsulfonamidepyridine 4.56 g (0.0132 mole) of 2-(O,O-isopropyliden-2,3-dihydroxypropoxy)-3-N,N-diethylsulfonamidepyridine are suspended in 45 mL of 1N hydrochloric acid and 20 mL of ethanol are added. The mixture is stirred at room temperature for 1 hour. Then it is evaporate "in vacuo" affording to an oil that is dried on potassium hydroxide and purified through a flash silica gel column chromatography using chloroform-methanol (9:1) as eluent. 3.71 g of the product required are obtained as a colourless oil. 92% yield.

Analysis for $C_{12}H_{20}N_2O_5S$: Theory %: C 47.36, H 6.62; N 9.20; S 10.53. Found %: C 47.51; H 6.52; N 9.23; S 10.78.

Ir (alkali halide disc): $\bar{\nu}$ (cm$^{-1}$) 3430 (very strong), 1582, 1560, 1430, 1325.

$^1$H-Nmr (DMSO-d$_6$): δ (ppm) 8.5–8.0 (part AB of the ABX system, 2H, 4—C$\underline{H}$, 6C$\underline{H}$); 7.12 (part X of the ABX system, 1H, 5—C$\underline{H}$); 4.8–4.6 (2m, 2H, OH, disappears on adding D$_2$O); 4.6–4.2 (m, 2H, OC$\underline{H}_2$); 4.2–3.4 (m, 3H, C$\underline{H}$OHC$\underline{H}_2$OH); 3.31 (q, 4H, NC$\underline{H}_2$CH$_3$); 1.02 (t, 6H, NC$\underline{H}_2$C$\underline{H}_3$).

EXAMPLE 9

2-(2-hydroxy-3-t-butylaminopropoxy)-3-N,N-dimethylsulfonamidepyridine 4.2 g (0.01 mole) of 2-(N,O-benzyliden-2-hydroxy-3-t-butylaminopropoxy)-3-N,N-dimethylsulfonamidepyridine are dissolved in a mixture of 26 mL of 1N hydrochloric acid and 10 mL of ethanol, being the whole mixture magnetically stirred at room temperature for 15 min. The reaction mixture is repeatedly washed with diethyl ether and the aqueous phase is neutralized with a saturated solution of sodium bicarbonate and extracted with chloroform. The solvent is evaporated "in vacuo". An oil is obtained and purified through flash silica gel column chromatography using chloroform-methanol (1:1) as eluent. 2.15 l g of a solid are obtained. m.p. 108°–109° C. (n-hexane). 65% yield.

Analysis for $C_{14}H_{25}N_3O_4S$: Theory %: C 50.74; H 7.60; N 12.68; S 9.67. Found %: C 50.88; H 7.58; N 12.76; S 9.88.

Ir (KBr): $\bar{\nu}$(cm$^{-1}$) 3400, 3150, 1575, 1562, 1455, 1415, 1325.

$^1$H-Nmr (CDCl$_3$): δ (ppm) 8.5–8.0 (part AB of the ABX system, 2H, 4—C$\underline{H}$, 6—C$\underline{H}$); 7.01 (part X of the ABX system, 1H, 5—C$\underline{H}$); 4.8–4.3 (m, 2H, OC$\underline{H}_2$); 4.3–3.7 (m, 1H, C$\underline{H}$OH); 3.0–2.4 (m, 4H, CH$_2$NH, OH disappears on adding D$_2$O); 2.87 (s, 6H, NC$\underline{H}_3$); 1.13 (s, 9H, C(CH$_3$)$_3$).

The corresponding maleate is obtained by treating 1.7 g (5.14 mole) of the base with 598 mg (5.15 mmole) of maleic acid in the minimum ethanol amount. By addition of diethyl ether to the mixture a precipitate of a colourless solid is obtained and crystallized from ethanol-diethyl ether. m.p. 113°–115° C.

Analysis for $C_{18}H_{29}N_3O_8S$: Theory %: C 48.31; H 6.53; N 9.39; S 7.16. Found %: C 48.56; H 6.50; N 9.49; S 7.27.

Ir (KBr): $\bar{\nu}$(cm$^{-1}$) 3600–2300, 1572, 1560, 1450, 1340.

$^1$H-Nmr (DMSO-d$_6$): δ (ppm) 7.8–8.8 (broad peak, 2H, NH$_2^+$, disappears on adding D$_2$O); 8.42, 8.13 (2dd, 2H, 4—C$\underline{H}$, 6—C$\underline{H}$); 7.14 (dd, 1H, 5—C$\underline{H}$), 6.00 (s, 2H, CH=C$\underline{H}$); 4.8–3.9 (m, 3H, ArOC$\underline{H}_2$C$\underline{H}$); 3.8–2.8 (m, 3$\underline{H}$, C$\underline{H}_2$NH$_2^+$, OH); 2.78 (s, 6H, NC$\underline{H}_3$); 1.30 (s, 9H, C(C$\underline{H}_3$)$_3$).

EXAMPLE 10

2-(2-hydroxy-3-t-butylaminopropoxy)-3-N,N-diethylsulfonamidepyridine 4.48 g (0.01 mole) of 2-(N,O-benzyliden-2-hydroxy-3-t-butylaminopropoxy)-3-N,N-diethylsulfonamidepyridine are dissolved in a mixture of 30 mL of 1N hydrochloric acid and 10 mL of ethanol and magnetically stirred at room temperature for 15 min. The reaction mixture is repeatedly washed with diethyl ether, the aqueous phase is neutralized with a saturated solution of sodium bicarbonate and extracted with cloroform. The solvent is evaporated "in vacuo", affording to an oil that is purified through flash silica gel column chromatography using chloroform-methanol (2:1) as eluent. 2.8 g of the product are obtained. m.p. 80°–81° C. (n-hexane). 78% yield.

Analysis for $C_{16}H_{29}N_3O_4S$: Theory %: C 53.46; H 8.13; N 11.69; S 8.92. Found %: C 53.61; H 8.17; N 11.61; S 9.25.

Ir (KBr): $\bar{\nu}$ (cm$^{-1}$) 3400, 3150, 1575, 1561, 1455, 1417, 1322.

$^1$H-Nmr (CDCl$_3$): δ (ppm) 8.4–8.1 (part AB of the ABX system, 2H,4—C$\underline{H}$, 6—1 C$\underline{H}$); 6.98 (part X of the ABX system, 1H, 5—C$\underline{H}$); 4.7–4.3 (m, 2H, OC$\underline{H}_2$); 4.3–3.6 (m, 1H, C$\underline{H}$OH), 3.37 (q, 4H, NC$\underline{H}_2$CH$_3$); 3.0–2.4 (m, 4H, C$\underline{H}_2$NH, O$\underline{H}$ disappears on adding D$_2$O); 1.12 (s,t, 15$\underline{H}$, NC$\underline{H}_2$C$\underline{H}_3$, C(C$\underline{H}_3$)$_3$).

The corresponding maleate is obtained by treating 2.8 g (7.8 mmole) of the base with 0.91 g (7.8 mmole) of maleic acid in 50 mL and a later addition of diethyl ether leads to a colourless precipitate that is again crystallized from ethanol-diethyl ether. m.p. 122°–123° C.

Analysis for C$_{20}$H$_{33}$N$_3$O$_8$S: Theory %: C 50.51; H 6.99; N 8.84; S 6.74. Found %: C 50.80; H 6.70; N 9.01; S 6.97.

Ir (KBr): $\bar{\nu}$ (cm$^{-1}$) 3600–2300, 1580, 1568, 1448, 1430, 1350.

$^1$H-Nmr (DMSO-d$_6$): δ (ppm) 8.4 (broad peak, 2H, NH$_2^+$); 8.39, 8.16 (2dd, 2H, 4—C$\underline{H}$, 6—C$\underline{H}$); 7.20 (dd, 1H, 5—C$\underline{H}$); 6.00 (s, 2H, CH=C$\underline{H}$); 4.8–3.9 (m, 3H, ArOC$\underline{H}_2$, $\underline{C}$H); 3.8–2.8 (m, 3$\underline{H}$, C$\underline{H}_2$NH$_2^+$, O$\underline{H}$); 3.30 (q, 4$\underline{H}$, NC$\underline{H}_2$CH$_3$); 1.29 (s, 9H, C(C$\underline{H}_3$)$_3$); 1.03 (t, 6H, NCH$_2$C$\underline{H}_3$).

We claim:

1. A compound of the formula

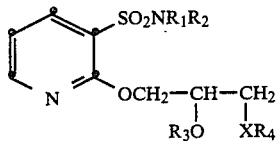

I wherein R$_1$ and R$_2$ represent a hydrogen atom or a lower alkyl group; R$_3$ and R$_4$ are hydrogen atoms or else form a five membered-ring with with two substituents R$_5$R$_6$C<, wherein R$_5$ and R$_6$ are independently hydrogen atoms, lower alkyl groups, or phenyl groups, and X represents an oxygen atom or a >N—R$_7$ group, R$_7$ being a C$_1$-C$_6$ alkyl group preferably branched out with isopropyl, isobuty, t-butyl, isoamyl, t-amyl, neopentyl groups.

2. The compound of claim 1 which is 2-(O,O-isopropyliden-2,3-dihydroxypropoxy)-3-sulfonamidepyridine.

3. The compound of claim 1 which is 2-(O,O-isopropyliden-2,3-dihydroxypropoxy)-3-N,N-dimethylsulfonamidepyridine.

4. The compound of claim 1 which is 2-(O,O-isopropyliden-2,3-dihydroxypropoxy)-3-N,N-diethylsulfonamidepyridine.

5. The compound of claim 1 which is 2-(N,O-benzyliden-2-hydroxy-3-t-butylaminopropoxy)-3-N,N-dimethylsulfonamidepyridine.

6. The compound of claim 1 which is 2-(N,O-benzyliden-2-hydroxy-3-t-butylaminopropoxy)-3-N,N-diethylsulfonamidepyridine.

7. The compound of claim 1 which is 2-(2,3-dihydroxypropoxy)-3-sulfonamidepyridine.

8. The compound of claim 1 which is 2-(2,3-dihydroxypropoxy)-3-N,N-dimethylsulfonamidepyridine.

9. The compound of claim 1 which is 2-(2,3-dihydroxypropoxy)-3-N,N-diethylsulfonamidepyridine.

10. The compound of claim 1 which is 2-(2-hydroxy-3-t-butylaminopropoxy)-3-N,N-dimethylsulfonamidepyridine.

11. The compound of claim 1 which is 2-(2-hydroxy-3-t-butylaminopropoxy)-3-N,N-diethylsulfonamidepyridine.

* * * * *